United States Patent
Ichihara et al.

(10) Patent No.: US 9,783,548 B2
(45) Date of Patent: Oct. 10, 2017

(54) PRODUCTION METHOD FOR EPOXY COMPOUND USING SOLID CATALYST

(71) Applicants: JX NIPPON OIL & ENERGY CORPORATION, Tokyo (JP); OSAKA UNIVERSITY, Osaka (JP)

(72) Inventors: Junko Ichihara, Osaka (JP); Shunro Yamaguchi, Osaka (JP); Atsushi Kameyama, Tokyo (JP); Takashi Suzuki, Tokyo (JP); Takashi Morikita, Tokyo (JP)

(73) Assignees: JX NIPPON OIL & ENERGY CORPORATION, Tokyo (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 15/038,107

(22) PCT Filed: Nov. 17, 2014

(86) PCT No.: PCT/JP2014/080375
§ 371 (c)(1),
(2) Date: Aug. 22, 2016

(87) PCT Pub. No.: WO2015/076222
PCT Pub. Date: May 28, 2015

(65) Prior Publication Data
US 2016/0347763 A1 Dec. 1, 2016

(30) Foreign Application Priority Data
Nov. 20, 2013 (JP) .................................. 2013-239919

(51) Int. Cl.
C07D 301/12 (2006.01)
C07D 301/03 (2006.01)
C07D 493/04 (2006.01)
B01J 23/30 (2006.01)

(52) U.S. Cl.
CPC ............ *C07D 493/04* (2013.01); *B01J 23/30* (2013.01); *C07D 301/12* (2013.01)

(58) Field of Classification Search
CPC ....... C07D 493/04; C07D 301/12; B01J 23/30
USPC .................................................. 549/523, 531
See application file for complete search history.

(56) References Cited

U.S. PATENT DOCUMENTS

| 5,430,161 A * | 7/1995 | Brown ..................... B01J 23/30 |
| | | 502/150 |
| 2010/0113807 A1* | 5/2010 | Ichihara ................ B01J 23/007 |
| | | 549/512 |

FOREIGN PATENT DOCUMENTS

| JP | S59-108793 A | 6/1984 |
| JP | S62-234550 A | 10/1987 |
| JP | 2002-059007 A | 2/2002 |
| JP | 2004-209449 | * 7/2004 |
| JP | 2004-209449 A | 7/2004 |
| JP | 2008-094916 A | 4/2008 |
| JP | 2010-235649 A | 10/2010 |
| JP | 2013241373 A | 12/2013 |
| JP | 2013241375 A | 12/2013 |
| JP | 2013241376 A | 12/2013 |
| JP | 5979631 B2 | 8/2016 |
| JP | 5979632 B2 | 8/2016 |
| JP | 5979633 B2 | 8/2016 |
| WO | 2008/093711 A1 | 8/2008 |

OTHER PUBLICATIONS

International Search Report and Written Opinion issued with respect to Application No. PCT/JP2014/080375 with mail date of Jan. 27, 2015.
International Preliminary Report on Patentability issued with respect to Application No. PCT/JP2014/080375 with mail date of Jun. 2, 2016.
Japanese Office Action issued with respect to Application No. P2013-239919, dated Apr. 4, 2017.

* cited by examiner

*Primary Examiner* — T. Victor Oh
(74) *Attorney, Agent, or Firm* — Greenblum & Bernstein, P.L.C.

(57) ABSTRACT

A method for producing an epoxy compound by reacting a compound having a carbon-carbon double bond with hydrogen peroxide in the coexistence of the compound having a carbon-carbon double bond, aqueous hydrogen peroxide, a powder of a solid catalyst support and a powder of a solid catalyst, wherein the solid catalyst comprises an isopolyacid, and the isopolyacid is produced from a catalyst raw material comprising (a) tungstic acid or a salt thereof and (b) at least one selected from the group consisting of a salt of an alkaline earth metal and a cationic polymer.

7 Claims, No Drawings

PRODUCTION METHOD FOR EPOXY COMPOUND USING SOLID CATALYST

TECHNICAL FIELD

The present invention relates to a method for producing epoxy compounds from compounds having a carbon-carbon double bond and hydrogen peroxide.

BACKGROUND ART

Epoxy compounds are reacted with various curing agents and curing catalysts to produce cured products. These epoxy compounds are useful as components of coating agents, adhesives, inks or sealants, or intermediates for producing other compounds which are useful in the various final applications such as pharmaceutical agents or medical products.

As a method for producing epoxy an compound, a method is known, in which olefins are epoxidized with peracids such as peacetic acid. However, this method has problems that peracids require careful handling, and epoxides are reacted with carboxylic acids presented in the reaction system thereby producing esters and the like, resulting in a decrease in the selectivity of the epoxides, and the post-treatments are troublesome. Therefore, a method has been attracting attention, which uses hydrogen peroxide as an oxidation agent, which is easy in handling and turns to water that is harmless after the reaction.

As a method for producing an epoxy compound from olefins using hydrogen peroxide, a method is known in which epoxidation is carried out by reacting olefins and a hydrogen peroxide solution with a halogenated hydrocarbon as a solvent using a catalyst such as polyacids (Patent Literature 1). This method, however, has problems concerning halogen impurities in the products and environmental load due to the use of the halogenated hydrocarbon.

Patent Literature 2 discloses a solid phase reaction system for oxidation comprising a mixture of a powdered solid catalyst support and a powdered solid catalyst for oxidation reaction, an organic compound and a hydrogen peroxide solution.

CITATION LIST

Patent Literature

Patent Literature 1: Japanese Patent Application Laid-Open Publication No. 62-234550
Patent Literature 2: WO 2008/093711

SUMMARY OF INVENTION

Technical Problem

An object of the present invention is to provide a method of performing the epoxidation of olefin compounds with good productivity.

Solution to Problem

The present invention relates to a method for producing an epoxy compound by reacting a compound having a carbon-carbon double bond with hydrogen peroxide in the coexistence of the compound having a carbon-carbon double bond, aqueous hydrogen peroxide, a powder of a solid catalyst support and a powder of a solid catalyst, wherein the solid catalyst comprises an isopolyacid, and the isopolyacid is produced from a catalyst raw material comprising (a) tungstic acid or a salt thereof and (b) at least one selected from the group consisting of a salt of an alkaline earth metal and a cationic polymer.

According to the present invention, since the isopolyacid in the solid catalyst is produced from a catalyst raw material comprising (a) tungstic acid or a salt thereof and (b) at least one selected from the group consisting of a salt of an alkaline earth metal and a cationic polymer, elution of the isopolyacid from the solid catalyst is sufficiently suppressed. For this reason, according to the present invention, an epoxy compound can be produced at high reaction rate and high yield, and isolation and recovery operations of the epoxy compound from a reaction mixture can be easily performed. In addition, the solid catalyst and the solid catalyst support after separation of the product can be re-used, and the present invention has advantages of stable qualities, stable operations of production facilities, reduction in producing costs, and reduction in waste materials such as spent catalysts, and in environmental impacts due to treatment of waste water.

The present invention also relates to the method for producing an epoxy compound, characterized in that the above catalyst raw material comprises ammonium tungstate.

The present invention also relates to the method for producing an epoxy compound, characterized in that the above catalyst raw material comprises at least one salt of an alkaline earth metal selected from the group consisting of Ca, Sr and Ba.

The present invention also relates to the method for producing an epoxy compound, characterized in that the above catalyst raw material comprises at least one cationic polymer selected from the group consisting of a salt of poly 4-vinylpyridine and a salt of poly N-alkyl-4-vinylpyridine.

The present invention also relates to the method for producing an epoxy compound, characterized in that the above compound having a carbon-carbon double bond is an alicyclic olefin compound.

The present invention also relates to the method for producing an epoxy compound, characterized in that the above compound having a carbon-carbon double bond is a compound represented by the following formula (2):

[Chemical Formula 1]

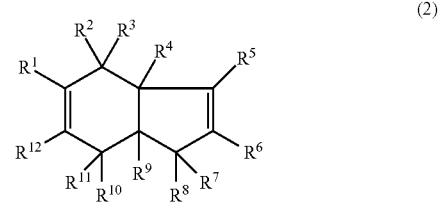

(2)

wherein $R^1$ to $R^{12}$ each independently represent a hydrogen atom, a halogen atom, an alkyl group that may have a substituent, or an alkoxy group that may have a substituent.

The present invention also relates to the method for producing an epoxy compound, characterized in that the above solid catalyst support is selected from the group consisting of phosphates, diatomaceous earth, silica, alumina, kaolin, silica alumina and calcium fluoride.

The present invention also relates to the method for producing an epoxy compound, characterized in that the above solid catalyst support is apatite.

Advantageous Effects of Invention

According to the present invention, a method for producing an epoxy compound, which makes it possible to produce an epoxy compound from a compound having a carbon-carbon double bond with good productivity is provided.

DESCRIPTION OF EMBODIMENTS

Preferable embodiments of the present invention will be described below.

The production method according to the present embodiment is a method for producing an epoxy compound by reacting a compound having a carbon-carbon double bond with hydrogen peroxide in the coexistence of the compound having a carbon-carbon double bond, aqueous hydrogen peroxide, a powder of a solid catalyst support and a powder of a solid catalyst.

In the present embodiment, the above solid catalyst comprises an isopolyacid. In addition, in the present embodiment, the above isopolyacid is an isopolyacid produced from a catalyst raw material comprising (a) tungstic acid or a salt thereof and (b) at least one selected from the group consisting of a salt of an alkaline earth metal and a cationic polymer.

According to the production method according to the present embodiment, an epoxy compound can be produced from a compound having a carbon-carbon double bond, with good productivity.

More specifically, in the production method according to the present embodiment, since the isopolyacid in the solid catalyst is produced from a catalyst raw material comprising (a) tungstic acid or a salt thereof (hereinafter, referred to as "component (a)" depending on cases) and (b) at least one selected from the group consisting of a salt of an alkaline earth metal and a cationic polymer (hereinafter, referred to as "component (b)" depending on cases), elution of the isopolyacid from the solid catalyst is sufficiently suppressed. For this reason, according to the production method according to the present embodiment, an epoxy compound can be produced at high reaction rate and high yield, and isolation and recovery operations of the epoxy compound from a reaction mixture can be easily performed.

In addition, in the present embodiment, since elution of the isopolyacid from the solid catalyst is sufficiently suppressed, the solid catalyst and the solid catalyst support after separation of the product can be re-used. For this reason, the production method according to the present embodiment has advantages of stable qualities, stable operations of production facilities, reduction in producing costs, and reduction in waste materials such as spent catalysts, and in environmental impacts due to treatment of waste water.

Examples of (a) tungstic acid or a salt thereof include $H_2WO_4$, $Na_2WO_4$, $NaHWO_4$, $(NH_4)_2WO_4$, $(NH_4)HWO_4$, $(NH_4)_6W_7O_{24}$, $(NH_4)_{10}[H_2W_{12}O_{42}]$, $[WO(O_2)_2(H_2O)_2]$, $K_2[WO(O_2)_2(H_2O)_2]_2O$, $Na_2[WO(O_2)_2(H_2O)_2]_2O$ and $K_4[W_{10}O_{32}]$.

As (a) tungstic acid or a salt thereof, ammonium tungstate such as $(NH_4)_{10}[H_2W_{12}O_{42}]$ may be suitably used.

The component (b) is selected from the group consisting of (b-1) a salt of an alkaline earth metal and (b-2) a cationic polymer.

(b-1) A salt of an alkaline earth metal is a salt comprising a cation of an alkaline earth metal, and Ca, Sr and Ba are suitably used as the alkaline earth metal. That is, (b-1) a salt of an alkaline earth metal may be at least one salt of an alkaline earth metal selected from the group consisting of Ca, Sr and Ba.

(b-1) A salt of an alkaline earth metal comprises an anion that ionic-bonds with an alkaline earth metal cation. The anion is not particularly limited, and examples of the anion include halide ions, nitrate ions, acetate ions, hydroxide ions, nitrite ions, and perchlorate ions. That is, (b-1) a salt of an alkaline earth metal may be, for example, halides, nitrates, acetates, hydroxides, nitrites and perchlorates of an alkaline earth metal. Among them, nitrates, acetates, halides and the like of an alkaline earth metal may be particularly suitably used as (b-1) a salt of an alkaline earth metal.

Specific examples of (b-1) a salt of an alkaline earth metal include calcium chloride (II), barium chloride (II), calcium nitrate (II), barium nitrate (II), calcium acetate (II), barium acetate (II), calcium hydroxide (II), barium hydroxide (II), calcium nitrite (II), barium nitrite (II), calcium perchlorate (II), and barium perchlorate (II). Among them, calcium nitrate (II), barium nitrate (II), calcium acetate (II), barium acetate (II), calcium chloride (II), and barium chloride (II) may be suitably used as (b-1) a salt of an alkaline earth metal.

It is preferable for an amount of (b-1) a salt of an alkaline earth metal used as the catalyst raw material be 0.5 mol % or more, and it is more preferable to be 1 mol % or more, with respect to the total amount of tungsten atom contained in the component (a). In addition, it is preferable for the amount of (b-1) a salt of an alkaline earth metal be 50 mol % or less, and it is more preferable to be 20 mol % or less.

(b-2) A cationic polymer may be said to be a polymer having a cationic functional group. Examples of the cationic functional group include a group having ammonium cation, and a group having pyridinium cation.

Examples of (b-2) a cationic polymer include a salt of poly 4-vinylpyridine, a salt of poly N-alkyl-4-vinylpyridine, a salt of poly 2-vinylpyridine, a salt of poly N-alkyl-2-vinylpyridine, and an anion exchange resin. Among them, a suitable (b-2) cationic polymer is a salt of poly 4-vinylpyridine, a salt of poly N-alkyl-4-vinylpyridine, a salt of poly 2-vinylpyridine, and a salt of poly N-alkyl-2-vinylpyridine, and a more suitable (b-2) cationic polymer is a salt of poly 4-vinylpyridine, and a salt of poly N-alkyl-4-vinylpyridine.

It is preferable for an amount of (b-2) a cationic polymer used as the catalyst raw material be 1 part by weight or more, and it is more preferable to be 5 parts by weight or more, with respect to 100 parts by weight of the component (a). In addition, it is preferable for the amount of (b-2) a cationic polymer to be 100 parts by weight or less, and it is more preferable to be 80 parts by weight or less, with respect to 100 parts by weight of the component (a).

An isopolyacid may be obtained, for example, by dissolving each of the components (a) and (b) in a solvent such as water, mixing the resultant, and isolating and purifying a salt precipitated from the mixed solution. The thus obtained isopolyacid may be used as a solid catalyst, as it is.

The catalyst raw material for obtaining an isopolyacid may further comprise components other than the components (a) and (b). For example, the catalyst raw material may further comprise a nitrogen-containing salt compound selected from the group consisting of a quaternary ammonium salt compound and a pyridinium salt compound. By using the above nitrogen-containing salt compound as the catalyst raw material, it is possible to further improve a reactivity of the solid catalyst.

An amount of a nitrogen-containing salt compound used as the catalyst raw material is preferably 0 to 90 mol % with respect to the total amount of tungsten atom contained in the component (a). In addition, it is preferable for the amount of the nitrogen-containing salt compound to be 10 mol % or more, and it is more preferable to be 20 mol % or more. With such an amount, effect due to the nitrogen-containing salt compound is more remarkably exhibited. In addition, it is preferable for the amount of the nitrogen-containing salt compound to be 90 mol % or less, and it is more preferable to be 80 mol % or less, with respect to the total amount of tungsten atom contained in the component (a). If the nitrogen-containing salt compound exists excessively, there is the case that elution of the isopolyacid from the solid catalyst occurs more easily as compared with the case of using no nitrogen-containing salt compound.

Examples of the quaternary ammonium salt compound include hydroxides, nitrates, sulfates, hydrogen sulfates, acetates, methosulfates, and ethosulfates of tetraalkylammoniums such as benzyltrimethylammonium, benzyltriethylammonium, benzyltributylammonium, phenyltrimethylammonium, tetrabutylammonium, tetrahexylammonium, tetraoctylammonium, trioctylmethylammonium, trioctylethylammonium, dilauryldimethylammonium, lauryltrimethylammonium, distearyldimethylammonium, stearyltrimethylammonium, dioctadecyldimethylammonium, octadecyltrimethylammonium, dicetyldimethylammonium, cetyltrimethylammonium, and tricaprylmethyl ammonium. In addition, the quaternary ammonium salt compound may be a compound which is prepared from naturally occurring raw materials, and has an unsaturated bond in part of an alkyl group, or has a distribution in the number of carbon atoms in an alkyl group. As the quaternary ammonium salt compound, a salt of cetyl trimethyl ammonium may be particularly suitably used.

Specific examples of the pyridinium salt compound include hydroxides, nitrates, sulfates, hydrogen sulfates, acetates, methosulfates, and ethosulfates of an alkylpyridinium such as dodecylpyridinium and cetylpyridinium. As the pyridinium salt compound, a salt of cetylpyridinium may be particularly suitably used.

The compound having a carbon-carbon double bond (hereinafter, referred to as an "olefin compound" depending on cases) is not particularly limited as long as the compound is a compound having one or more carbon-carbon double bonds in the molecule.

Examples of the olefin compound include ethylene; mono-substituted olefins such as propylene, 1-butene, 1-pentene, 4,4-dimethyl-1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-octadecene, 3,3-dimethyl-1-butene, vinylcyclopentane, vinylcyclohexane, allylcyclohexane, styrene, 4-(tert-butyl) styrene, allylbenzene, 4-methoxystyrene, safrole, eugenol, and 3,4-dimethoxy-1-allylbenzene; di-substituted olefins such as 2-butene, isobutylene, 2-methyl-1-butene, 2-pentene, 2-hexene, 2-methyl-1-hexene, 3-hexene, 2-heptene, 2-methyl-1-heptene, 3-heptene, 2-octene, 3-octene, 4-octene, 2-nonene, 2-methyl-2-nonene, 3-nonene, 4-nonene, 5-decene, 2-methyl-1-undecene, cyclopentene, cyclohexene, 4-methyl cyclohexene, cycloheptene, cyclooctene, cyclodecene, cyclododecene, methylenecyclohexane, β-methylstyrene, stilbene, isosafrole, isoeugenol, β-pinene, and norbornene; tri-substituted olefins such as 2-methyl-2-butene, 2-methyl-2-pentene, 2-methyl-2-hexene, 2,5-dimethyl-2,4-hexadiene, 2-methyl-2-heptene, 1-methylcyclopentene, 1-methylcyclohexene, 1-(tert-butyl)cyclohexene, 1-isopropylcyclohexene, 2-carene, 3-carene, and α-pinene; and tetra-substituted olefins such as 2,3-dimethyl-2-butene, and 2,3,4-trimethyl-2-pentene.

In the present embodiment, as the olefin compound, an alicyclic olefin compound may be suitably used, and an alicyclic olefin compound represented by the following formula (2) may be more suitably used. In the production method according to the present embodiment, in one aspect thereof, the alicyclic epoxy compound represented by the formula (1) may be obtained by performing epoxidation of the compound represented by the formula (2).

[Chemical Formula 2]

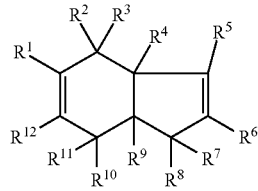
(2)

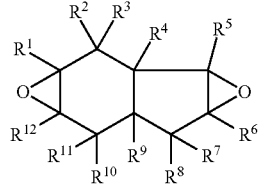
(1)

In formulas (1) and (2), $R^1$, $R^2$, $R^3$, $R^4$, $R^5$, $R^6$, $R^7$, $R^8$, $R^9$, $R^{10}$, $R^{11}$ and $R^{12}$ are each independently a hydrogen atom, a halogen atom, an alkyl group which may have a substituent, or an alkoxy group which may have a substituent.

The alkyl group is preferably an alkyl group having 1 to 10 carbon atoms, more preferably an alkyl group having 1 to 4 carbon atoms. The expression "may have a substituent" indicates that part or all of hydrogen atoms possessed by the alkyl group may be substituted by group other than a hydrogen atom. Examples of the substituent include a halogen atom (preferably a chlorine atom or a fluorine atom, and more preferably a fluorine atom), and an alkoxy group (preferably an alkoxy group having 1 to 10 carbon atoms, and more preferably an alkoxy group having 1 to 3 carbon atoms).

The alkoxy group is preferably an alkoxy group having 1 to 10 carbon atoms, more preferably an alkoxy group having 1 to 4 carbon atoms. The expression "may have a substituent" indicates that part or all of hydrogen atoms possessed by the alkoxy group may be substituted by group other than a hydrogen atom. Examples of the substituent include a halogen atom (preferably a chlorine atom or a fluorine atom, and more preferably a fluorine atom), and an alkoxy group (preferably an alkoxy group having 1 to 10 carbon atoms, and more preferably an alkoxy group having 1 to 3 carbon atoms).

$R^1$ to $R^{12}$ are each independently preferably, a hydrogen atom, a fluorine atom, an alkyl group or an alkoxy group, more preferably a hydrogen atom or a fluorine atom, more preferably a hydrogen atom.

That is, as the alicyclic olefin compound represented by the formula (2), a compound represented by the following formula (4) is preferably used, and an alicyclic diepoxy compound represented by the following formula (3) is obtained according to epoxidation of a compound represented by the formula (4).

[Chemical Formula 3]

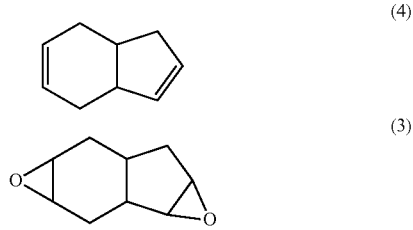

The solid catalyst support may be powders of solid materials having properties that they disperse a solid catalyst, a hydrogen peroxide solution and a compound having a carbon-carbon double bond, are not degraded thereby and do not disturb the oxidation reaction (epoxidation reaction), preferably those having properties to facilitate the oxidation reaction. Specific examples include phosphates such as apatite, clays such as diatomaceous earth [main component: silica], kaolin [main component: silica-alumina] and hydrotalcite, fluorides such as calcium fluoride, and oxides such as silica, titania and alumina. Among these, a solid catalyst support selected from phosphates, diatomaceous earth, silica, alumina, kaolin, silica-alumina and calcium fluoride is preferably used because they can achieve a higher yield. In particular, a solid catalyst support selected from apatite, diatomaceous earth and calcium fluoride can achieve a particularly higher yield.

Herein, the apatite is a kind of calcium phosphate, and fluorapatite, chlorapatite, carbonate apatite and hydroxyapatite exist as apatite-type minerals. Among these, bydroxyapatite and fluorapatite are preferably used.

The diatomaceous earth is a soft rock or soil composed mainly of a husk of Bacillariophyta, and contains silica as a main component but also often alumina, ferric oxide, alkali metal oxides in addition to silica. Alternatively, those which are porous and have a high porosity and a cake bulk density of about 0.2 to 0.45 are often used. Among diatomaceous earths, calcined products or freshwater diatomaceous earths are preferred but other diatomaceous earths may be used. Specific examples of such diatomaceous earths include those marketed under the tradename of Celite (registered trademark) by Celite Corporation and marketed under the tradename of Celatom by Eagle Pitcher Minerals, Inc. Alternatively, those calcined together with sodium carbonate may also be used.

The solid catalyst is not required to be immobilized to the solid catalyst support, and all what needs to be done is that the powdered solid catalyst is simply mixed with the powdered solid catalyst support. For example, the powdered solid catalyst is added in advance to the powdered solid catalyst support and then stirred and mixed thereby producing a mixture of the solid catalyst and solid catalyst support. No particular limitation is imposed on the particle sizes of the powdered solid catalyst and powdered solid catalyst support. Those having a particle size of about 5 to 100 µm, which are easily available may be used thereby achieving the advantageous effects of the present invention such as a higher yield of the product.

It is preferable for an amount of the solid catalyst to be 5 to 100 parts by mass, and more preferably 10 to 80 parts by mass, with respect to 100 parts by mass of the total amount of the solid catalyst support. If the amount is 5 parts by mass or more, a reaction speed of the epoxidation reaction is improved, and the epoxy compound can be obtained with better yield. On the other hand, if the amount is in a range exceeding 80 parts by mass, the yield is not improved even though the amount of the solid catalyst is increased, resulting in industrial disadvantage.

In addition, it is preferable for a total amount of the solid catalyst support and the solid catalyst to be in the range of about 0.01 to 5 g, and more preferably 0.02 to 3.0 g, with respect to 1 mmol of the compound having a carbon-carbon double bond.

In the present embodiment, it is preferable for a tungsten content in the solid catalyst (a content of tungsten atom) to be 1 to 25 parts by mass, and it is more preferable to be 2 to 20 parts by mass, with respect to 100 parts by mass of the total amount of the solid catalyst and the solid catalyst support. If the tungsten content is 1 part by mass or more, a reaction speed of the epoxidation reaction is improved, and the epoxy compound can be obtained with better yield. On the other hand, if the tungsten content is in a range exceeding 25 parts by mass, a ring-opening reaction of epoxy easily proceeds, resulting in low yield.

The above tungsten content may be determined, for example, by measuring a tungsten content in a mixture of the solid catalyst support and the solid catalyst. The tungsten content in a mixture of the solid catalyst support and the solid catalyst may be measured by pre-treating a mixture of the solid catalyst support and the solid catalyst with alkali fusion, and thereafter performing an inductively coupled plasma emission (ICP emission) analysis. As a measuring device, for example, Optima4300DV of PerkinElmer Inc., etc. may be used.

A hydrogen peroxide concentration of aqueous hydrogen peroxide is preferably 5 to 60 mass %. In the case of using a hydrogen peroxide solution of a low concentration in a method for producing an epoxy compound using hydrogen peroxide, the produced epoxide is hydrolyzed to produce by-products such as diols and the like, resulting in the reduced selectivity of the intended product. However, the method of the present embodiment is high in selectivity and can produce the intended product at a higher yield even in the case of using a hydrogen peroxide solution of low concentration.

The amount of aqueous hydrogen peroxide added may be made to be in the range of about 0.5 to 5 mmol as hydrogen peroxide, preferably 0.6 to 2.5 mmol, with respect to 1 mmol of the double bond site in the compound having a carbon-carbon double bond. If the amount is less than 0.5 mmol, there is the case that the yield of an epoxy compound is decreased due to the shortage of hydrogen peroxide and, if the amount exceeds 5 mmol, the ring-opening reaction is likely to occur, resulting in the decrease in the yield of an epoxy compound. In particular, in the case of producing a compound of the formula (1), if the amount of hydrogen peroxide exceeds 5 mmol, a tendency wherein the yield of an epoxy compound decreases becomes remarkable.

In the present embodiment, the epoxidation may be performed by adding the compound having a carbon-carbon double bond and aqueous hydrogen peroxide to a mixture of a powder of the solid catalyst support and a powder of the solid catalyst. This addition is performed such that the both (the compound having a carbon-carbon double bond and aqueous hydrogen peroxide) are dispersed in the mixture and contact with each other, but, for example, mixing and stirring may be performed after the addition, so as for the both to be well dispersed and well contact with each other. Thereafter, the reaction may be performed in a state of standing this mixture, or the reaction may be performed while mixing or stirring is carried out.

In the present embodiment, an organic solvent may be further added to the mixed powder of the solid catalyst support and the solid catalyst, before, after or simultaneously with adding thereto the compound having a carbon-carbon double bond and aqueous hydrogen peroxide. The use of the organic solvent can restrain epoxides and water from contacting mutually so as to be likely to avoid the produced epoxides from ring-opening. It is preferable for an amount of the organic solvent added to be 500 parts by mass or less with respect to 100 parts by mass of the total amount of the compound having a carbon-carbon double bond. If the amount of the organic solvent exceeds 500 parts by mass, there is the tendency that the reaction speed becomes slow, and that the yield of the epoxy compound decreases.

As a type of the organic solvent, alcohols, ethers, esters, ketones, nitriles, amides, sulfones, epoxies, aliphatic compounds, aromatic compounds, etc. may be used. Preferable organic solvents are ethanol, ethyl acetate, hexane, toluene, etc., and toluene is particularly preferable.

In the present embodiment, it is preferable for a reaction temperature of the oxidation reaction (epoxidation reaction) to be 0 to 50° C., and it is more preferable to be 5 to 40° C. If the reaction temperature is too low, there is the tendency that a progress of the reaction becomes slow and, if the reaction temperature is too high, there is the case that the solid catalyst loses its activity, or that the yield decreases owing to the ring-opening of the epoxy.

In the present embodiment, it is preferable for a reaction time of the oxidation reaction to be 1 to 24 hours, and it is more preferable to be 1 to 12 hours. If the reaction time is too short, there is the case that the reaction does not proceed sufficiently and the yield decreases and, if the reaction time is too long, the production efficiency decreases.

In the present embodiment, a conversion ratio of the olefin compound due to epoxidation is preferably 80% or more. In addition, in the present embodiment, yield of the epoxy compound is preferably 50% or more.

No particular limitation is imposed on the method for isolating the epoxy compound. For example, a method may be used wherein the epoxy compound is solvent-extracted and then concentrated. In addition, the obtained epoxy compound may be also purified by known purification methods.

The chlorine content of the epoxy compound produced by the present embodiment is preferably 100 ppm by mass or less, more preferably 10 ppm by mass or less because the compound when formed into a cured resin product can be further improved in moisture proof reliability. The chlorine content is the value measured in accordance with JIS K-7243-3, specifically the value measured by dissolving an epoxy compound in diethylene glycol monobutyl ether and saponifying the solution with a potassium hydroxide alcohol solution, heating it to reflux, followed by potentiometric titration with a silver nitrate solution. The chlorine content of the epoxy compound can be reduced by purification by distillation, or alternatively by a method such as alkali aqueous solution washing or absorbent treatment.

The metal content of the epoxy compound produced by the present embodiment is preferably 100 ppm by mass or less, more preferably 10 ppm by mass or less because a cured resin product produced from the compound is further enhanced in mechanical characteristics and electrical characteristics. The metal content can be measured by analyzing a 10% toluene solution of an epoxy compound with inductively-coupled plasma emission (ICP emission). The apparatus for the measurement may be Optima 4300DV manufactured by Perkin-Elmer Corp. In this measurement, quantitative analysis of each metal species detected by qualitative analysis can be carried out using a commercially available metal standard solution. The metal content of the epoxy compound can be reduced by purification by distillation, or alternatively by a method such as alkali aqueous solution washing or absorbent treatment.

In the above, the suitable embodiments of the present invention are described, but the present invention is not limited to the above embodiments.

EXAMPLES

The present invention will be described in more detail with the following examples but is not limited thereto.

Production Example 1: Production of Solid Catalyst 1

16 g (5.0 mmol) of ammonium paratungstate tetrahydrate and 0.16 g (0.60 mmol) of barium nitrate (II) were added to 650 ml of water, heated to 65° C. and dissolved to obtain a first aqueous solution. 14 g (40 mmol) of cetylpyridinium chloride monohydrate was added to 250 ml of water, heated to 35° C. and dissolved to obtain a second aqueous solution. While the first aqueous solution was stirred at room temperature, the second aqueous solution was added to the first aqueous solution, and stirred at room temperature for 30 minutes. The resulting white suspension was filtered, washed with 700 ml of water. The obtained solid was dried at room temperature under reduced pressure to obtain 27 g of a white solid. This was defined as Solid Catalyst 1.

Production Example 2: Production of Solid Catalyst 2

16 g (5.0 mmol) of ammonium paratungstate tetrahydrate was added to 650 ml of water, heated to 65° C. and dissolved to obtain a first aqueous solution. 14 g (40 mmol) of cetylpyridinium chloride monohydrate and 1.6 g (6.0 mmol) of barium nitrate (II) were added to 250 ml of water, heated to 35° C. and dissolved to obtain a second aqueous solution. While the first aqueous solution was stirred at room temperature, the second aqueous solution was added to the first aqueous solution, and stirred at room temperature for 30 minutes. The resulting white suspension was filtered, washed with 700 ml of water. The obtained solid was dried at room temperature under reduced pressure to obtain 27 g of a white solid. This was defined as Solid Catalyst 2.

Production Example 3: Production of Solid Catalyst 3

16 g (5.0 mmol) of ammonium paratungstate tetrahydrate was added to 650 ml of water, heated to 65° C. and dissolved to obtain a first aqueous solution. 14 g (40 mmol) of cetylpyridinium chloride monohydrate and 3.1 g (12 mmol) of barium nitrate (II) were added to 250 ml of water, heated to 35° C. and dissolved to obtain a second aqueous solution. While the first aqueous solution was stirred at room temperature, the second aqueous solution was added to the first aqueous solution, and stirred at room temperature for 30 minutes. The resulting white suspension was filtered, washed with 700 ml of water. The obtained solid was dried at room temperature under reduced pressure to obtain 27 g of a white solid. This was defined as Solid Catalyst 3.

Production Example 4: Production of Solid Catalyst 4

16 g (5.0 mmol) of ammonium paratungstate tetrahydrate and 0.16 g (1.0 mmol) of calcium nitrate (II) were added to 650 ml of water, heated to 65° C. and dissolved to obtain a first aqueous solution. 14 g (40 mmol) of cetylpyridinium chloride monohydrate was added to 250 ml of water, heated to 35° C. and dissolved to obtain a second aqueous solution. While the first aqueous solution was stirred at room temperature, the second aqueous solution was added to the first aqueous solution, and stirred at room temperature for 30 minutes. The resulting white suspension was filtered, washed with 700 ml of water. The obtained solid was dried at room temperature under reduced pressure to obtain 27 g of a white solid. This was defined as Solid Catalyst 4.

Production Example 5: Production of Solid Catalyst 5

0.67 g (0.21 mmol) of ammonium paratungstate tetrahydrate was added to 34 ml of water, stirred at room temperature and dissolved to obtain a first aqueous solution. 0.77 g (1.9 mmol) of cetyltrimethylammonium methosulfate was added to 24 ml of water, heated to 35° C. and dissolved to obtain a second aqueous solution. 0.067 g of poly 4-vinylpyridine was added to 0.65 ml of water. While stirring this, 0.11 g of 20% sulfuric acid was added dropwise. The insoluble matter was removed by filtration to obtain a third solution. The second solution and the third solution were mixed with each other to obtain a fourth solution. While the first aqueous solution was stirred at room temperature, the fourth aqueous solution was added to the first aqueous solution, and stirred at room temperature for 30 minutes. The resulting white suspension was filtered and washed with 10 ml of water. The obtained solid was dried at room temperature under reduced pressure to obtain 1.1 g of a white solid. This was defined as Solid Catalyst 5.

Production Example 6: Production of Solid Catalyst 6

3.1 g (1.0 mmol) of ammonium paratungstate tetrahydrate was added to 160 ml of water, heated to 35° C. and dissolved to obtain a first aqueous solution. 3.8 g (9.5 mmol) of cetyl trimethyl ammonium methosulfate was added to a solvent consisting of 60 ml of methanol and 40 ml of water, and dissolved at room temperature to obtain a second aqueous solution. While the first aqueous solution was stirred at room temperature, the second aqueous solution was added to the first aqueous solution, and stirred at room temperature for 12 hours. The resulting white suspension was filtered, and washed with 50 ml of methanol, followed by twice washing with 50 ml of water. The obtained white solid was dried at room temperature under reduced pressure to obtain 4.5 g of a white solid. This was defined as Solid Catalyst 6.

(Analysis Method of a Tungsten Content in the Mixture of a Solid Catalyst Support and a Solid Catalyst)

In the following Examples and Comparative Example, the tungsten content in a mixture of the solid catalyst support and the solid catalyst was measured by pre-treating the mixture of the solid catalyst support and the solid catalyst with alkali fusion and, thereafter performing an inductively coupled plasma emission (ICP emission) analysis. As a measuring device, Optima4300DV of PerkinElmer Inc. was used.

Example 1

In a screw-cap test tube, 1.0 g of apatite that is a solid catalyst support, and 0.15 g of Solid Catalyst 1 were weighed, and mixed well with each other. As a result of ICP analysis of the mixture, the tungsten content was 59 mg. To the mixture were added 0.61 g of toluene, 1.2 g (10 mmol) of tetrahydroindene, and 1.7 g (18 mmol) of 35% aqueous hydrogen peroxide. After stirring at 20° C. for 6 hours, the reaction mixture was extracted with toluene (1 mL×3 times). The solvent was distilled off from the extract to obtain a crude product. The crude product was charged in a still, and distillation was performed under pressure of 2 mmHg. As a fraction of a column top temperature of 90° C., 0.81 g of tetrahydroindene diepoxide was obtained. The yield of the product (the yield of the diepoxide) was 53%. In addition, as a result of ICP analysis of the mixture of the solid catalyst support and the solid catalyst, which was a residue in the extraction, the tungsten content was 45 mg.

Example 2

Except that Solid Catalyst 1 in Example 1 was replaced with Solid Catalyst 2, an epoxidation reaction was performed in the same method as in Example 1. A tungsten content in the mixture of the solid catalyst support and the solid catalyst before the reaction was 59 mg, and a tungsten content in the mixture of the solid catalyst support and the solid catalyst (in a residue in the extraction) after the reaction was 47 mg. The amount of tetrahydroindene diepoxide obtained was 0.71 g, and the yield was 47%.

Example 3

Except that Solid Catalyst 1 in Example 1 was replaced with Solid Catalyst 3, an epoxidation reaction was performed in the same method as in Example 1. A tungsten content in the mixture of the solid catalyst support and the solid catalyst before the reaction was 61 mg, and a tungsten content in the mixture of the solid catalyst support and the solid catalyst (in a residue in the extraction) after the reaction was 52 mg. The amount of tetrahydroindene diepoxide obtained was 0.61 g, and the yield was 40%.

Example 4

Except that Solid Catalyst 1 in Example 1 was replaced with Solid Catalyst 4, an epoxidation reaction was performed in the same method as in Example 1. A tungsten content in the mixture of the solid catalyst support and the solid catalyst before the reaction was 57 mg, and a tungsten content in the mixture of the solid catalyst support and the solid catalyst (in a residue in the extraction) after the reaction was 42 mg. The amount of tetrahydroindene diepoxide obtained was 0.81 g, and the yield was 53%.

Example 5

Except that Solid Catalyst 1 in Example 1 was replaced with Solid Catalyst 5, an epoxidation reaction was performed in the same method as in Example 1. A tungsten content in the mixture of the solid catalyst support and the solid catalyst before the reaction was 58 mg, and a tungsten content in the mixture of the solid catalyst support and the solid catalyst (in a residue in the extraction) after the reaction was 46 mg. The amount of tetrahydroindene diepoxide obtained was 0.59 g, and the yield was 39%.

Comparative Example 1

Except that Solid Catalyst 1 in Example 1 was replaced with Solid Catalyst 6, an epoxidation reaction was performed in the same method as in Example 1. A tungsten content in the mixture of the solid catalyst support and the solid catalyst before the reaction was 59 mg, and a tungsten content in the mixture of the solid catalyst support and the solid catalyst (in a residue in the extraction) after the reaction was 40 mg. The amount of tetrahydroindene diepoxide obtained was 0.58 g, and the yield was 38%.

The yield (the yield of tetrahydroindene diepoxide) and a tungsten residual ratio (a ratio of a tungsten content after the reaction to a tungsten content before the reaction) in Examples 1 to 5 are shown in Table 1. The tungsten residual ratio was calculated by the following equation:

Tungsten residual ratio (%)=(tungsten content in the mixture of the solid catalyst support and the solid catalyst after the reaction)×100/(tungsten content in the mixture of the solid catalyst support and the solid catalyst before the reaction)

TABLE 1

| | Example 1 | Example 2 | Example 3 | Example 4 | Example 5 | Comparative Example 1 |
|---|---|---|---|---|---|---|
| Solid catalyst | Solid catalyst 1 | Solid catalyst 2 | Solid catalyst 3 | Solid catalyst 4 | Solid catalyst 5 | Solid catalyst 6 |
| Yield (%) | 53 | 47 | 40 | 53 | 39 | 38 |
| Tungsten residual ratio (%) | 77 | 79 | 84 | 73 | 79 | 67 |

INDUSTRIAL APPLICABILITY

According to the present invention, an epoxy compound can be produced with good productivity.

The invention claimed is:

1. A method for producing an epoxy compound comprising:
reacting a compound having a carbon-carbon double bond with hydrogen peroxide in the coexistence of the compound having a carbon-carbon double bond, aqueous hydrogen peroxide, a powder of a solid catalyst support and a powder of a solid catalyst,
wherein the solid catalyst comprises an isopolyacid, and the isopolyacid is produced from a catalyst raw material comprising (a) tungstic acid or a salt thereof and (b) a cationic polymer.

2. The method according to claim 1, wherein the catalyst raw material comprises an ammonium tungstate.

3. The method according to claim 1, wherein the catalyst raw material comprises at least one cationic polymer selected from the group consisting of a salt of poly 4-vinylpyridine and a salt of poly N-alkyl-4-vinylpyridine.

4. The method according to claim 1, wherein the compound having a carbon-carbon double bond is an alicyclic olefin compound.

5. The method according to claim 1, wherein the compound having a carbon-carbon double bond is a compound represented by the following formula (2):

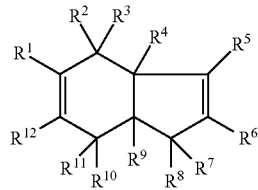

(2)

wherein $R^1$ to $R^{12}$ each independently represent a hydrogen atom, a halogen atom, an alkyl group that may have a substituent selected from the group consisting of a halogen atom and an alkoxy group, or an alkoxy group that may have a substituent selected from the group consisting of a halogen atom and an alkoxy group.

6. The method according to claim 1, wherein the solid catalyst support is selected from the group consisting of phosphates, diatomaceous earth, silica, alumina, kaolin, silica alumina and calcium fluoride.

7. The method according to claim 1, wherein the solid catalyst support is apatite.

* * * * *